(12) United States Patent
Piron et al.

(10) Patent No.: US 10,592,857 B2
(45) Date of Patent: Mar. 17, 2020

(54) SYSTEM AND METHOD FOR MANAGING EQUIPMENT IN A MEDICAL PROCEDURE

(71) Applicants: Cameron Piron, Toronto (CA); Joshua Richmond, Toronto (CA)

(72) Inventors: Cameron Piron, Toronto (CA); Joshua Richmond, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 247 days.

(21) Appl. No.: 15/503,335

(22) PCT Filed: Aug. 15, 2014

(86) PCT No.: PCT/CA2014/050781
§ 371 (c)(1),
(2) Date: Feb. 10, 2017

(87) PCT Pub. No.: WO2016/023097
PCT Pub. Date: Feb. 18, 2016

(65) Prior Publication Data
US 2017/0243157 A1 Aug. 24, 2017

(51) Int. Cl.
| G06Q 10/08 | (2012.01) |
| G06Q 50/22 | (2018.01) |
| A61B 34/20 | (2016.01) |
| A61B 90/00 | (2016.01) |
| A61B 90/98 | (2016.01) |
| G06F 19/00 | (2018.01) |

(52) U.S. Cl.
CPC .......... *G06Q 10/087* (2013.01); *A61B 34/20* (2016.02); *A61B 90/361* (2016.02); *A61B 90/98* (2016.02); *G06Q 50/22* (2013.01); *A61B 2034/2057* (2016.02); *A61B 2090/0804* (2016.02); *A61B 2090/373* (2016.02); *G06F 19/321* (2013.01)

(58) Field of Classification Search
None
See application file for complete search history.

(56) References Cited

U.S. PATENT DOCUMENTS

| 7,382,255 | B2 * | 6/2008 | Chung | ............... | G06K 7/10346 340/572.1 |
| 7,617,137 | B2 * | 11/2009 | Kreiner | ............... | G06Q 10/087 705/28 |
| 8,600,478 | B2 * | 12/2013 | Verard | ............... | A61B 5/06 600/424 |
| 9,002,083 | B2 * | 4/2015 | Fox | ............... | G06F 19/3418 382/128 |
| 2005/0182296 | A1 * | 8/2005 | Furukawa | ............... | A61B 1/00055 600/118 |

(Continued)

*Primary Examiner* — Michael Tomaszewski
(74) *Attorney, Agent, or Firm* — Ridout & Maybee LLP

(57) ABSTRACT

An electronic device is provided including a processor, an input device coupled to the processor, a memory coupled to the processor; and a module saved in the memory. The module configures the processor to, during a procedure phase of a medical procedure, identify pieces of equipment to be used in the medical procedure using input from the input device; track the pieces of equipment being used in the medical procedure using input from the input device; and account for each of the pieces of equipment at completion of the medical procedure using input from the input device.

12 Claims, 13 Drawing Sheets

(56) References Cited

U.S. PATENT DOCUMENTS

| | | | | |
|---|---|---|---|---|
| 2006/0145871 | A1* | 7/2006 | Donati | B65D 23/00 340/572.8 |
| 2007/0078678 | A1* | 4/2007 | DiSilvestro | G06Q 50/22 705/2 |
| 2007/0112649 | A1* | 5/2007 | Schlabach | G06Q 10/087 705/28 |
| 2007/0125392 | A1* | 6/2007 | Olson, Jr. | A61B 90/90 128/899 |
| 2009/0317002 | A1* | 12/2009 | Dein | A61B 50/362 382/224 |
| 2009/0326336 | A1* | 12/2009 | Lemke | G06F 19/3481 600/300 |
| 2010/0046791 | A1* | 2/2010 | Glickman | G06K 9/209 382/100 |
| 2010/0138238 | A1* | 6/2010 | Sobie | G06Q 10/087 705/3 |
| 2010/0217623 | A1* | 8/2010 | Schoenberg | G06Q 50/22 705/3 |
| 2010/0252626 | A1* | 10/2010 | Elizondo | G06Q 10/087 235/385 |
| 2010/0324933 | A1* | 12/2010 | Giap | G06Q 10/08 705/3 |
| 2013/0339039 | A1* | 12/2013 | Roman | G06Q 50/22 705/2 |
| 2015/0120321 | A1* | 4/2015 | David | G06Q 50/22 705/2 |
| 2015/0173843 | A1* | 6/2015 | Maughan | A61B 17/80 705/3 |
| 2016/0179198 | A1* | 6/2016 | Levesque | G06F 3/016 340/407.1 |
| 2016/0212577 | A1* | 7/2016 | Dor | G06F 16/2379 |

* cited by examiner

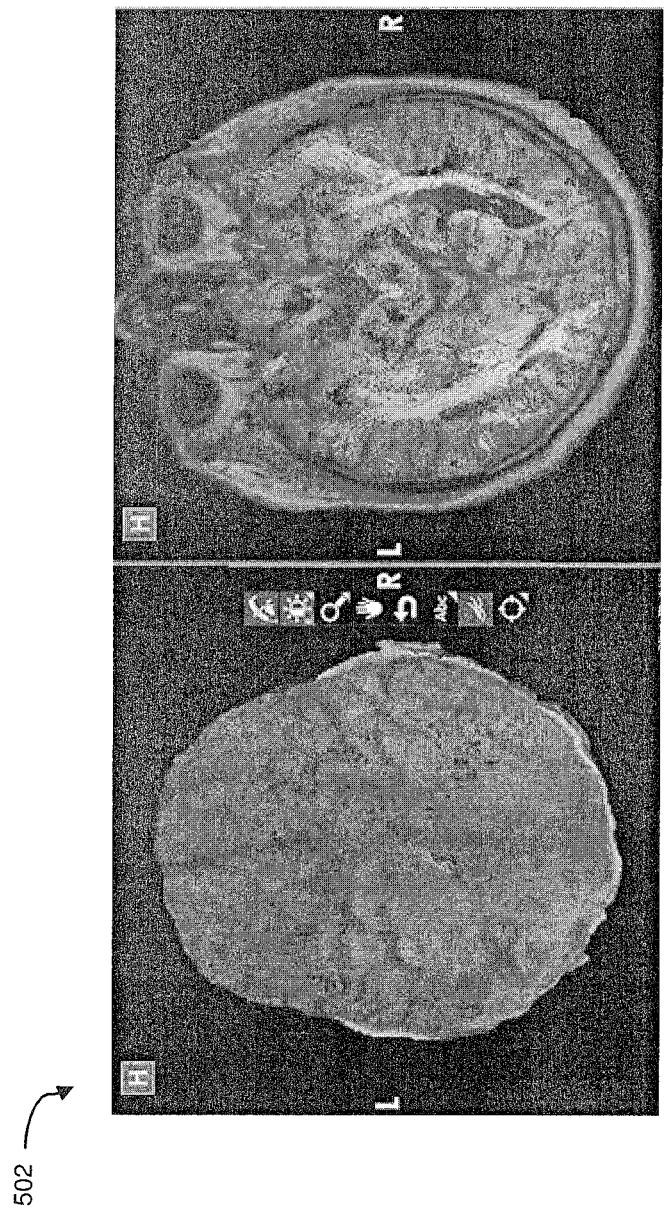
Figure 5A: Review Step

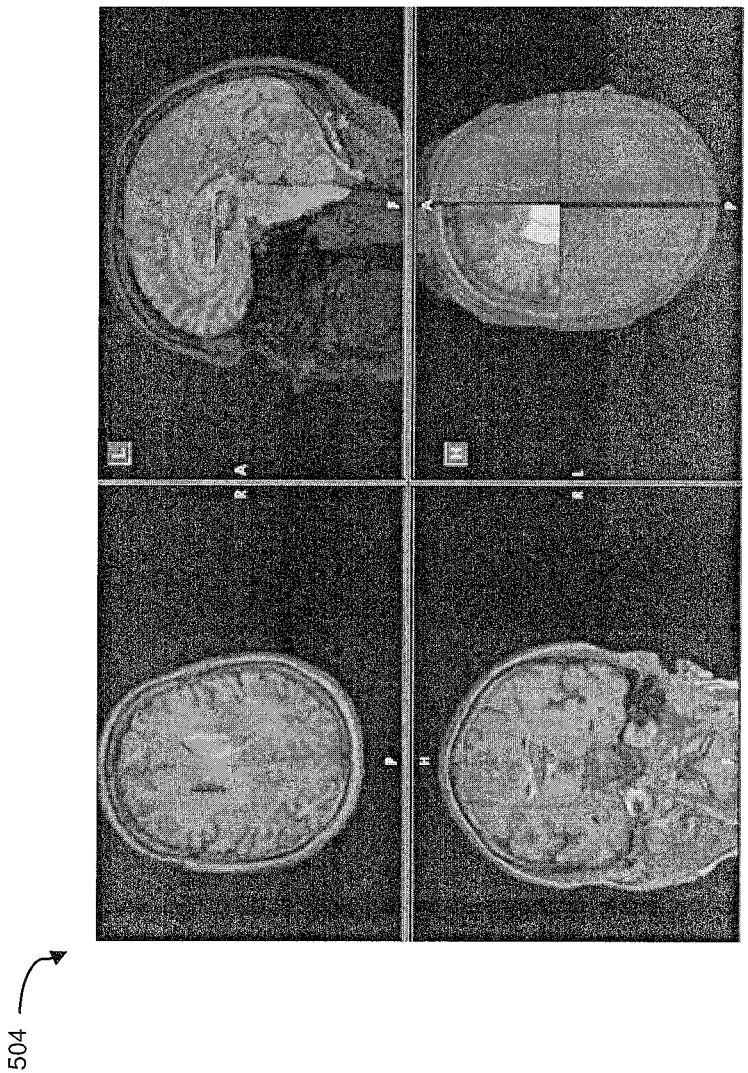
Figure 5B: Regions Step

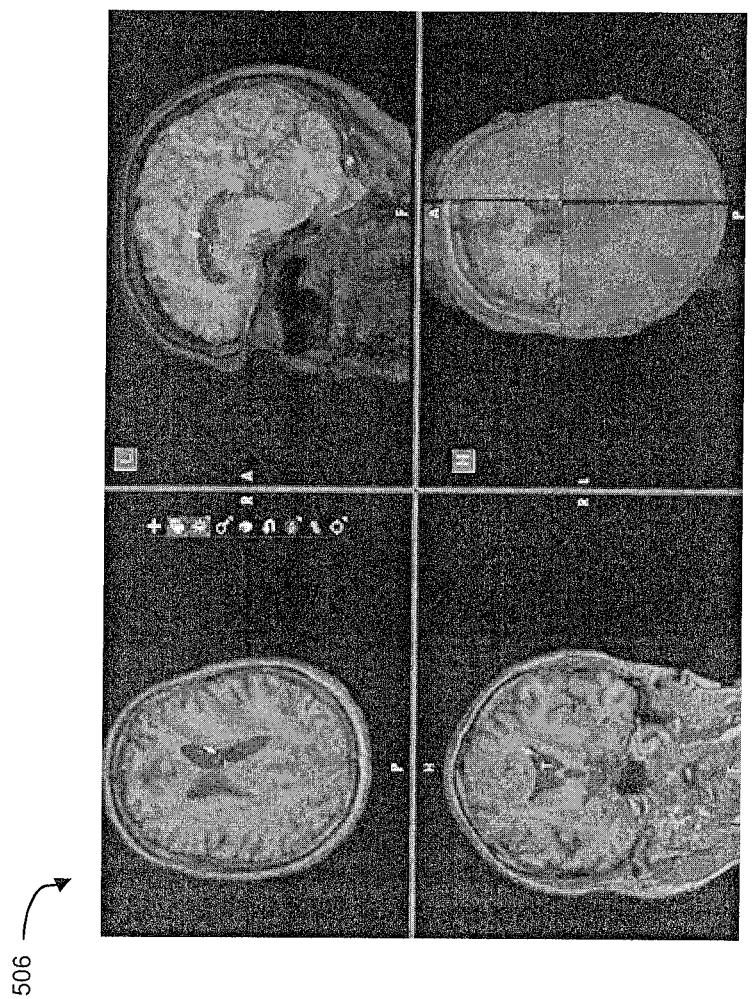
Figure 5C: Targets Step

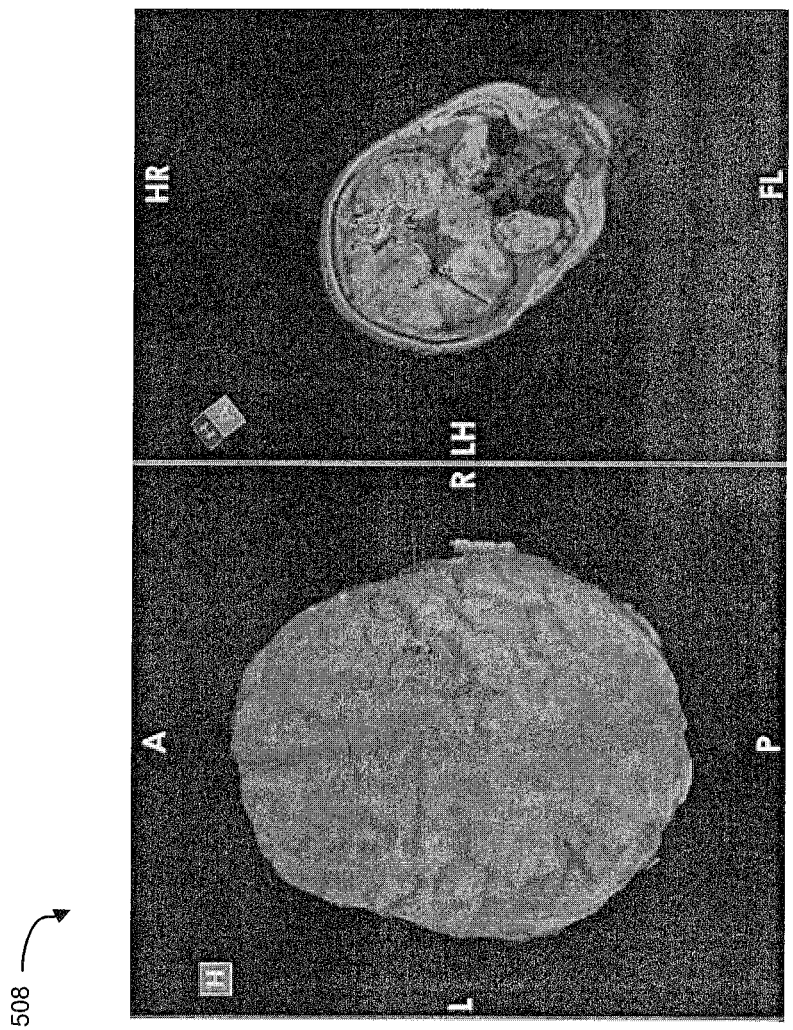
Figure 5D: Trajectory Step

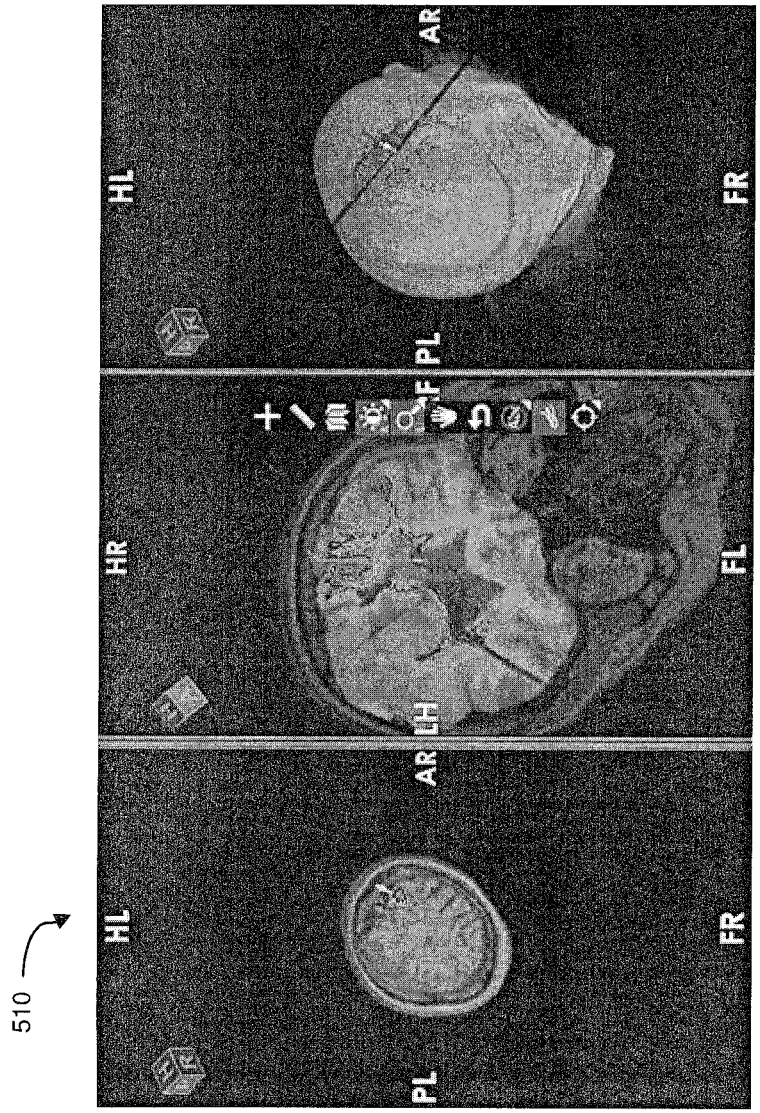
Figure 5E: Sulci Path Step

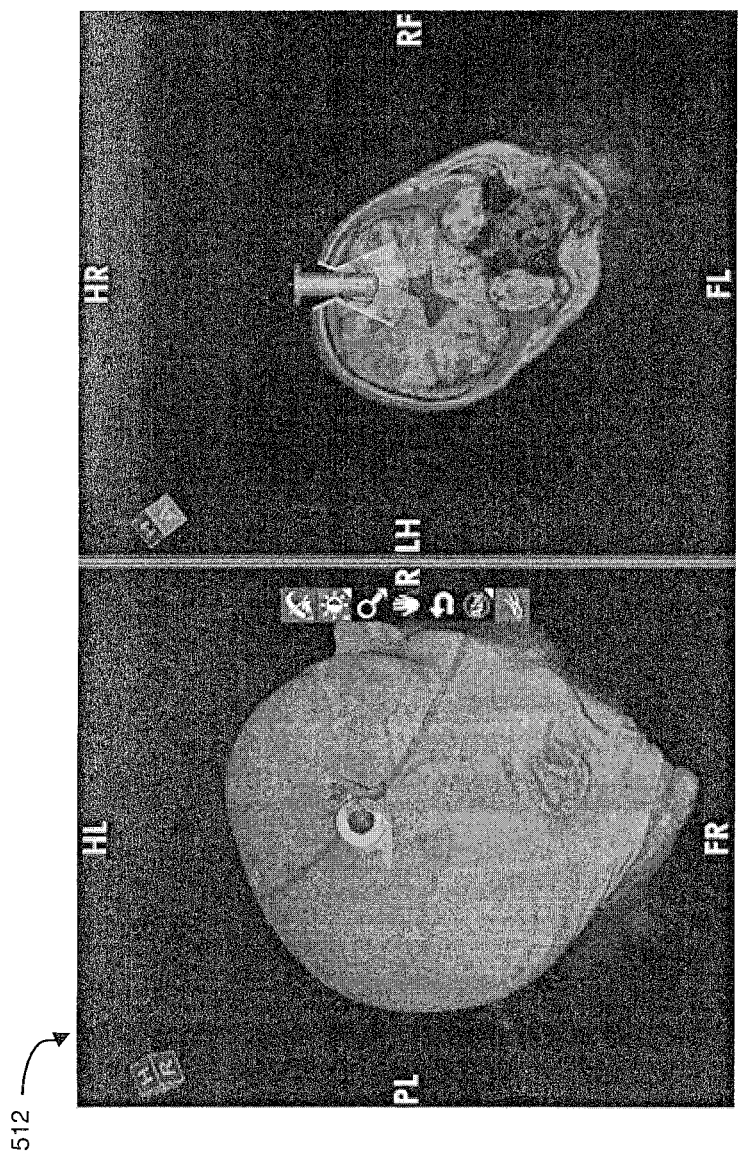
Figure 5F: Craniotomy Step

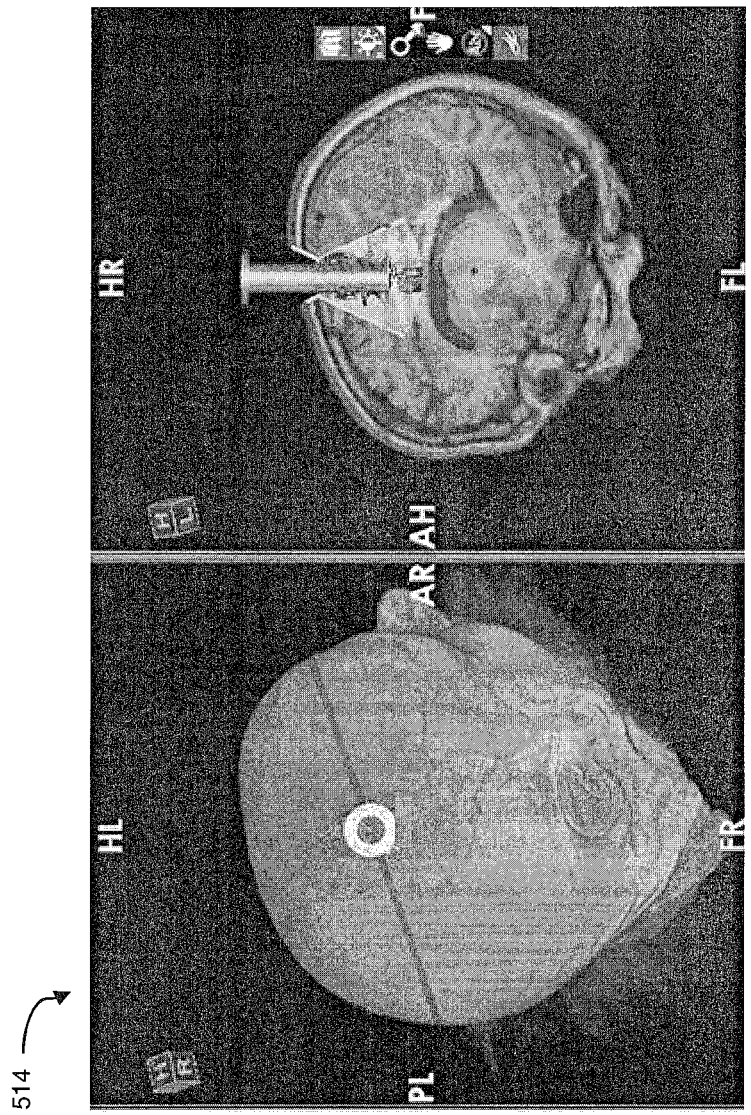
Figure 5G: Export Step

SYSTEM AND METHOD FOR MANAGING EQUIPMENT IN A MEDICAL PROCEDURE

FIELD

The present disclosure generally relates to automated tools for surgery, and more specifically, to a system and method for managing equipment in a medical procedure.

BACKGROUND

Traditionally, brain tumors and intracranial hemorrhages (ICH) are treated by removing most of the top half of the patient's skull and resecting healthy white matter to get to the tumor or ICH of interest. This approach has the disadvantages of: permanent removal of healthy white matter; increased trauma to the brain via de-pressurization after removal of a large portion of the skull; and long recovery time due to large cranial trauma.

The neurosurgeon is typically guided in these procedures using a navigation system that displays the position of surgical tools overlaid on pre-surgical Magnetic Resonance (MR) or Computed Tomography (CT) images in real-time. In these procedures, one or more targets and a surgical path are defined. An ideal surgical path will be determined by the surgeon before the surgery but is not encoded or reflected by the navigation system.

Referring to FIG. 1A, an exemplary navigation system 100 is shown to support minimally invasive access port-based surgery. In FIG. 1A, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during his procedure. An operator 103 is also present to operate, control and provide assistance for the navigation system 100.

Once a procedure is planned with a planning system, a logistics coordinator is required to prepare an operating room prior to a surgical procedure, which can take as long as three hours. A lack of the correct tools and consumables during surgery can cause the surgical team to compromise the procedure. Additionally, sometimes counting parts and tools in and out of the surgical field results in counting errors and missing parts.

Thus, there is a need for a system and method to manage equipment and provide the equipment to the neurosurgeon that will lead to the most informed and least damaging trajectory during surgical procedures.

SUMMARY

This disclosure describes a system and method for managing equipment in a medical procedure.

One aspect of the present description provides an electronic device including a processor, an input device coupled to the processor, a memory coupled to the processor; and a module saved in the memory. The module configures the processor to, during a procedure phase of a medical procedure, identify pieces of equipment to be used in the medical procedure using input from the input device; track the pieces of equipment being used in the medical procedure using input from the input device; and account for each of the pieces of equipment at completion of the medical procedure using input from the input device. The input device may include a tracking camera, an optical camera, RFID receiver, a structured light camera, or a stereo camera pair.

The module may further configure the processor to: based on a medical procedure plan generated during a planning phase of the medical procedure and prior to the procedure phase: generate an equipment list for completing the medical procedure; check the generated equipment list with equipment on hand at a facility where the medical procedure will be performed; and automatically generate an order for equipment not on hand at the facility where the medical procedure will be performed.

Another aspect of the present description provides a method of managing equipment for medical procedure, the method including, during a procedure phase of a medical procedure: identifying pieces of equipment to be used in the medical procedure based on input from an input device; tracking the pieces of equipment being used in the medical procedure based on input from the input device; and accounting for each of the pieces of equipment at completion of the medical procedure based on input from the input device. The input device may include a tracking camera, an optical camera, RFID receiver, a structured light camera, or a stereo camera pair. The method may further include, based on a medical procedure plan generated during a planning phase of the medical procedure and prior to the procedure phase: generating an equipment list for completing the medical procedure; checking the generated equipment list with equipment on hand at a facility where the medical procedure will be performed; and automatically generating an order for equipment not on hand at the facility where the medical procedure will be performed.

A further understanding of various aspects of the subject matter can be realized by reference to the following detailed description and drawings.

BRIEF DESCRIPTION OF THE DRAWINGS

In order that the subject matter may be readily understood, embodiments are illustrated by way of examples in the accompanying drawings, in which:

FIGS. 5A-5G are exemplary screenshots illustrating the planning method of FIG. 4;

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses or processes will be described below to provide examples of embodiments of the navigation method and system disclosed herein. No embodiment described below limits any claimed embodiment and any claimed embodiments may cover processes or apparatuses that differ from those described below. The claimed embodiments are not limited to apparatuses or processes having all of the features of any one apparatus or process described below or to features common to multiple or all of the apparatuses or processes described below. It is possible that an apparatus or process described below is not an embodiment of any claimed subject matter.

Furthermore, numerous specific details are set forth in order to provide a thorough understanding of the embodiments described herein. However, it will be understood by those skilled in the relevant arts that the embodiments described herein may be practiced without these specific details. In other instances, well-known methods, procedures and components have not been described in detail so as not to obscure the embodiments described herein.

Figure 1:
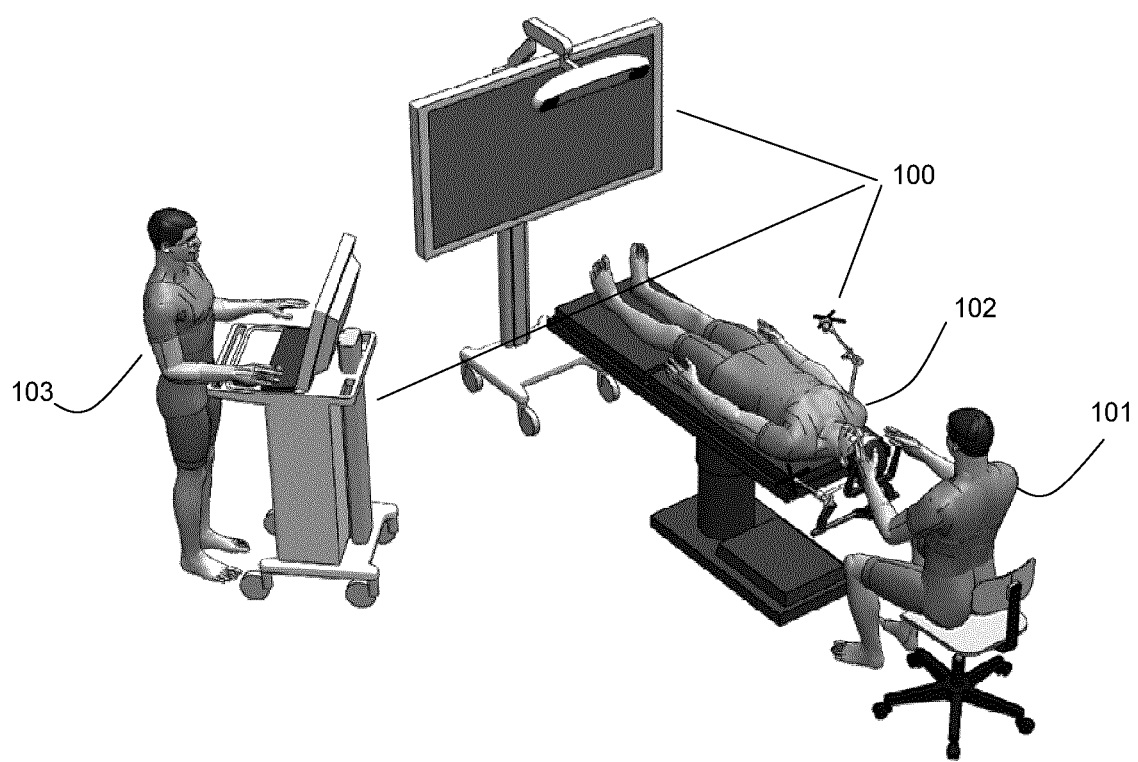
FIG. 1 shows an exemplary operating room setup for a minimally invasive access port-based medical procedure.
Figure 2:
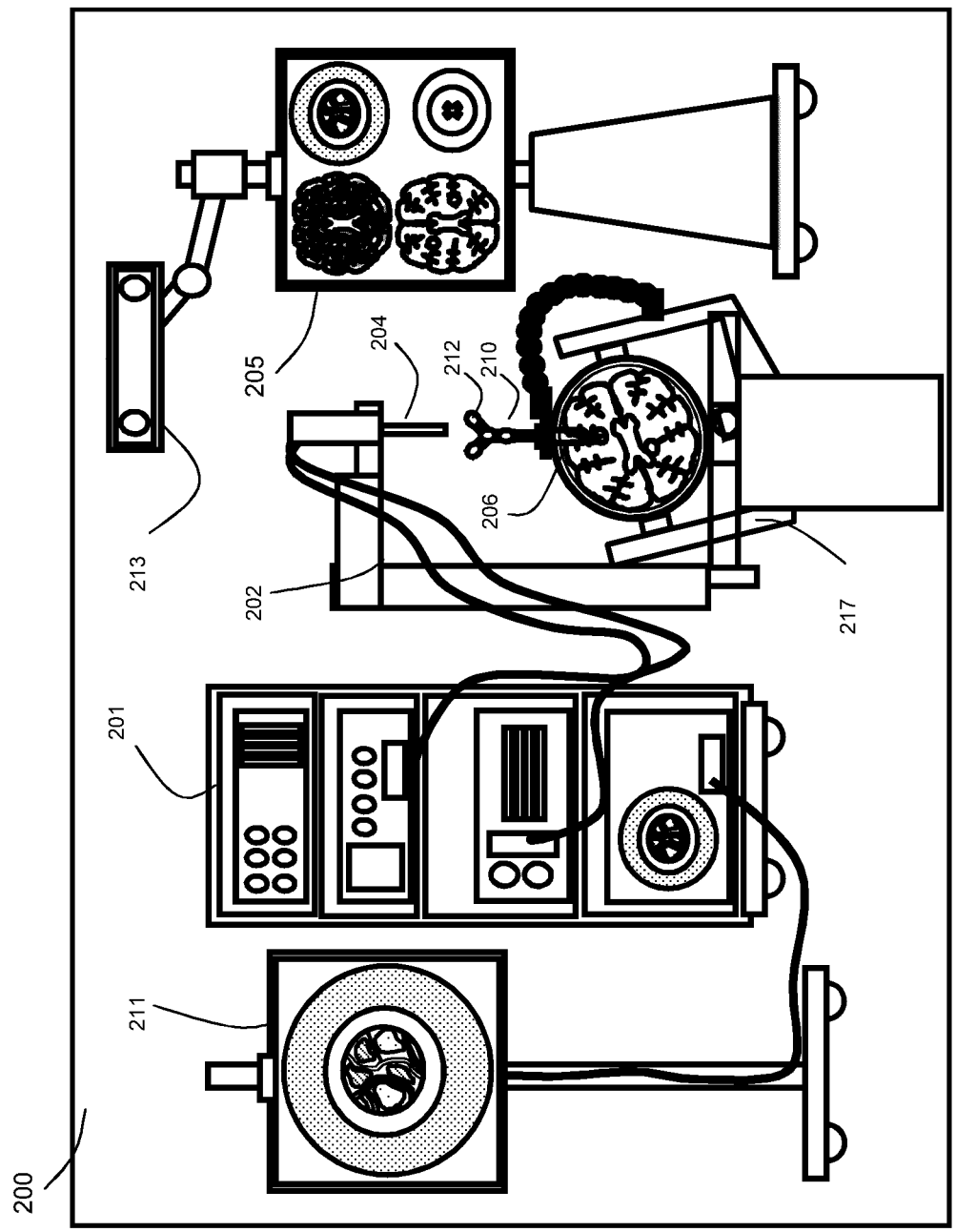
FIG. 2 is a block diagram illustrating components of a medical navigation system that may be used to implement a surgical plan for a minimally invasive surgical procedure.

Referring to FIG. 2, a block diagram is shown illustrating components of an exemplary medical navigation system 200. The medical navigation system 200 illustrates the context in which a surgical plan including equipment (e.g., tool and material) tracking, such as that described herein, may be implemented. The medical navigation system 200 includes one or more monitors 205, 211 for displaying a video image, an equipment tower 201, and a mechanical arm 202, which supports an optical scope 204. The equipment tower 201 is mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example, the equipment tower 201 may be a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example, the tracking camera 213 may be a 3D optical tracking stereo camera, similar to one made by Northern Digital Imaging (NDI), configured to locate reflective sphere tracking markers 212 in 3D space. In another example, the tracking camera 213 may be a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example, the output may be shown in axial, sagittal and coronal views as part of a multi-view display.

As noted above with reference to FIG. 2, the introducer 210 may include tracking markers 212 for tracking. The tracking markers 212 may be reflective spheres in the case of an optical tracking system or pick-up coils in the case of an electromagnetic tracking system. The tracking markers 212 are detected by the tracking camera 213 and their respective positions are inferred by the tracking software.

Figure 3:
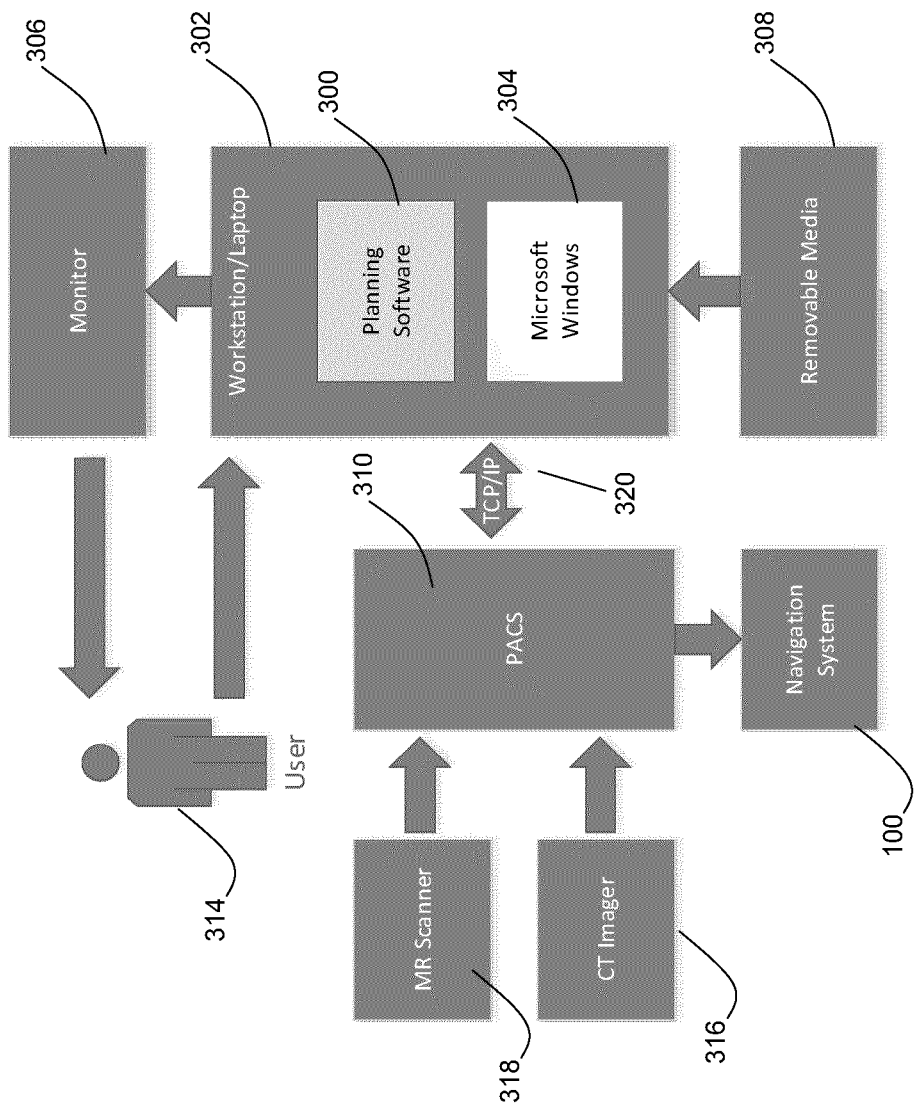
FIG. 3 is a block diagram illustrating components of a planning system used to plan a medical procedure that may then be implemented using the navigation system of FIG. 2.

Referring to FIG. 3, a block diagram is shown illustrating a planning module 300 used for a medical procedure suitable for implementing a method for planning a medical procedure according to various aspects of the present description. As shown in FIG. 3, the planning module 300 may be installed on a computing device 302. In one example, the computing device 302 may be a personal computer suitably configured to operate in a hospital environment. In one example, the planning module 300 may be a software module installed on the computing device 302. In one example, the computing device 302 may run an operating system 304 such as the Microsoft Windows operation system. The computing device 302 may be a workstation computer, laptop, tablet, mobile device, wearable computer device, or any other suitable computing device. While in one example, the operating system 304 of the computing device 302 may be Microsoft Windows, other operating systems such as Apple OSX, Linux, QNX, iOS, Android, or BlackBerry OS may also be used.

The computing device 302 may be connected to one or more display monitor(s) 306, where the output data is shown to a user 314. The user 314 may be a nurse, the operator 103, the neurosurgeon 101, or a user of the planning module 300 running on the computing device 302. The computing device 302 may also receive input from removable media 308. The removable media 308 may include a CD-ROM, Blu-Ray disk, USB memory stick, external hard drive, or other memory storage devices.

The planning module 300 may aim to make the planning of procedures more effective and efficient than in current practice. The planning module 300 running on the computing device 302 may also interface with a picture archiving and communication system (PACS) 310, typically over a TCP/IP network 320 communication interface. The PACS 310 may receive input from an MR scanner 318 in the form of MR Images, or from a CT imager 316 in the form of CAT scans. As shown in FIG. 3, PACS 310 interfaces with 2 sources of image data (MR and CT), but other sources of image data such as Optical Coherence Tomography (OCT), Positron Emission Tomography (PET), Ultra Sound (US) may be used. The PACS 310 interfaces with the navigation system 100 where the output of planning module 300 may be considered as the initial input to the navigation system 100 to be used in a medical procedure. While the planning module 300 is shown installed on computing device 302 and navigation system 100 is shown as a separate block in FIG. 3, in some embodiments the computing device 302 may be part of the navigation system 100 and the planning system and navigation system may function using the same computing device.

In addition to port-based procedures, the planning module 300 may also be used to support planning of functional Deep Brain Stimulation (DBS) procedures, neural biopsy procedures, and/or catheter or shunt placement. In all these cases, the procedure involves delivering a surgical device to a target location along a trajectory. Additionally, the planning module 300 may be used to support any suitable type of surgical procedure.

Figure 4:
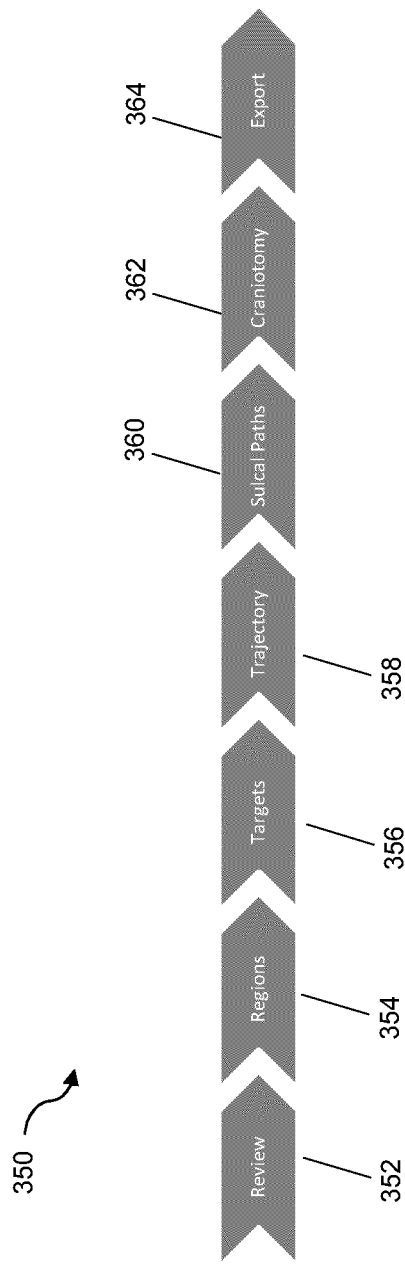
FIG. 4 is a flow chart illustrating a method for planning one type of medical procedure using the planning system of FIG. 3.

Referring to FIG. 4, a flow chart is shown illustrating a method 350 for planning a medical procedure, for example using the planning system of FIG. 3. FIG. 4 is discussed in combination with FIGS. 5A-5G, which show exemplary screenshots that may be provided when executing the blocks of method 350. In one example, the method 350 illustrates the steps executed by planning module 300 to generate a planned medical procedure. In one example, the planned medical procedure may be a surgical procedure, but could also be any suitable type of procedure, whether for diagnosis or treatment.

The planning module 300 may execute a number steps in the method 350, the first of which may include a review block 352. At the review block 352, a review phase is provided in which a user interface model may be generated for accepting data such as brain mask, diffusion, and tractography data available for study. FIG. 5A shows an exemplary screen shot 502 that may be provided by the planning module 300 during the review block 352.

Next, at a block 354, a regions phase is provided, which allows regions of interest in clinical images to be defined to aid in development of a surgical plan. The regions phase at block 354 may provide a user interface model for annotating volumes of interest within the primary image series, as well as co-registered Fractional Anisotropy (FA) and Apparent Diffusion Coefficient (ADC) image series, if they are available. The volumes of interest may aid in visualizing and placing candidate target locations within subsequent blocks of the method 350. FIG. 5B illustrates an exemplary screen shot 504 of regions phase 354.

Next, at a block 356, a targets phase is provided. The targets phase at block 356 may provide a user interface model for visualizing and placing target locations in and around tumor locations. A target location is the endpoint of a surgical cannulation using a brain path. FIG. 5C illustrates an exemplary screen shot 506 of the targets phase provided at the block 356.

Next, at a block 358, a trajectory phase is provided, which identifies target and engagement points to define intended trajectories to approach pathology regions. The trajectory phase provided at the block 358 may provide a user interface model for placing points of entry from a location on the surface of the brain to a target location in order to form a trajectory, for example for a surgical cannulation using a brain path. Block 358 may also provide a scorecard user interface model to provide comparisons between trajectory characteristics to this point in the workflow. FIG. 5D illustrates an exemplary a screen shot 508 of the trajectory phase provided at the block 358.

Next, at a block 360, the sulcal paths phase is provided. The sulcal paths phase at the block 360 may provide a user interface model for visualizing and placing waypoints for a surgical cannulation along a trajectory from engagement point to target, typically along a sulcal path. The sulcal paths phase at the block 360 may allow the user to segment the path through the sulcus and evaluate how this path might differ from the theoretical direct trajectory. FIG. 5E illustrates an exemplary screen shot 510 of the sulcal paths phase provided at the block 360.

Next, at a block 362, a craniotomy phase is provided, which may provide the ability to define a preferred dimension for craniotomy using regions of interest, target and/or engagement points. In the craniotomy phase provided at the block 362, a user interface model may be provided for estimating the location and size of the craniotomy required to support a trajectory for surgical cannulation using a brain path. FIG. 5F illustrates an exemplary screen shot 512 of the craniotomy phrase provided at the block 362.

Next, at a block 364, an export phase may provide an interface model for reviewing and exporting one or more trajectory plans as an image series to a PACS for subsequent use in suitable surgical navigation systems, such as the medical navigation system 200 shown in FIG. 2. FIG. 5G illustrates an exemplary screen shot 514 of the export phase provided by the block 364.

In one example, the latter four blocks 358, 360, 362, 364 may provide the user with a scorecard user interface model to provide comparisons between trajectory characteristics to this point in the workflow. In another example, the regions phase provided by the block 354, the sulcal paths phase provide by the block 360, and the craniotomy phase provided by the block 362 may be considered optional and may be omitted in certain plans.

Figure 6:
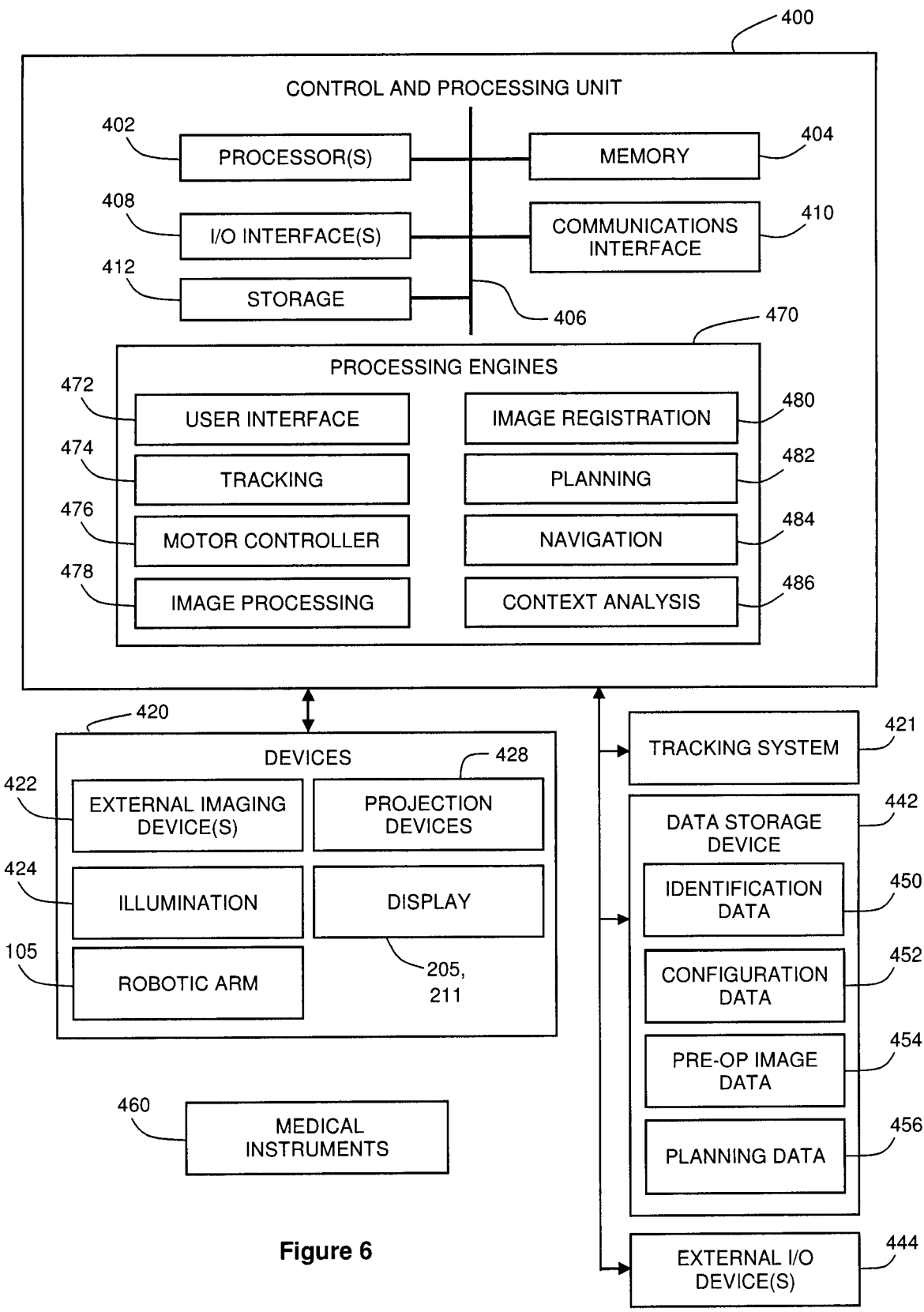
FIG. 6 is a block diagram illustrating a control and processing system that may be used in the planning system shown in FIG. 3 and the navigation system shown in FIG. 2.

Referring to FIG. 6, a block diagram is shown illustrating a control and processing system 400 that may be used in either the planning system 300 shown in FIG. 3 or the navigation system 200 shown in FIG. 2. As shown in FIG. 6, in one embodiment, control and processing system 400 may include one or more processors 402, a memory 404, a system bus 406, one or more input/output interfaces 408, a communications interface 410, and storage device 412. Control and processing system 400 may be interfaced with other external devices, such as tracking system 421, data storage 442, and external user input and output devices 444, which may include, for example, one or more of a display, keyboard, mouse, foot pedal, microphone and speaker. Data storage 442 may be any suitable data storage device, such as a local or remote computing device (e.g. a computer, hard drive, digital media device, or server) having a database stored thereon. In the example shown in FIG. 6, data storage device 442 includes identification data 450 for identifying one or more medical instruments 460 and configuration data 452 that associates customized configuration parameters with one or more medical instruments 460. Data storage device 442 may also include preoperative image data 454 and/or medical procedure planning data 456. Although data storage device 442 is shown as a single device in FIG. 6, it will be understood that in other embodiments, data storage device 442 may be provided as multiple storage devices.

In a further embodiment, various 3D volumes, at different resolutions, may each be captured with a unique time-stamp and/or quality metric. This data structure provides an ability to move through contrast, scale and time during the procedure and may also be stored in data storage device 442.

Medical instruments 460 are identifiable by control and processing unit 400. Medical instruments 460 may be connected to and controlled by control and processing unit 400, or medical instruments 460 may be operated or otherwise employed independent of control and processing unit 400. Tracking system 421 may be employed to track one or more of medical instruments and spatially register the one or more tracked medical instruments to an intraoperative reference frame. Tracking system 421 may include the tracking camera 213 shown in FIG. 2.

Control and processing unit 400 may also interface with a number of configurable devices, and may intraoperatively reconfigure one or more of such devices based on configuration parameters obtained from configuration data 452. Examples of devices 420, as shown in FIG. 6, include one or more external imaging devices 422, one or more illumination devices 424, the robotic arm 105, one or more projection devices 428, and one or more displays 205, 211.

Exemplary aspects of the disclosure can be implemented via processor(s) 402 and/or memory 404. For example, the functionalities described herein can be partially implemented via hardware logic in processor 402 and partially using the instructions stored in memory 404, as one or more processing modules or engines 470. Example processing modules include, but are not limited to, user interface engine 472, tracking module 474, motor controller 476, image processing engine 478, image registration engine 480, procedure planning engine 482, navigation engine 484, and context analysis module 486. While the example processing modules are shown separately in FIG. 6, in one example the processing modules 470 may be stored in the memory 404 and the processing modules may be collectively referred to as processing modules 470.

It is to be understood that the system is not intended to be limited to the components shown in FIG. 6. One or more components of the control and processing system 400 may be provided as an external component or device. In one alternative embodiment, navigation module 484 may be provided as an external navigation system that is integrated with control and processing system 400.

Some embodiments may be implemented using processor 402 without additional instructions stored in memory 404. Some embodiments may be implemented using the instructions stored in memory 404 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

The example embodiments described herein describe systems and methods in which a device is intraoperatively configured based on the identification of a medical instrument. In other example embodiments, one or more devices may be automatically controlled and/or configured by determining one or more context measures associated with a medical procedure. A "context measure", as used herein, refers to an identifier, data element, parameter or other form of information that pertains to the current state of a medical procedure. In one example, a context measure may describe, identify, or be associated with the current phase or step of the medical procedure. In another example, a context measure may identify the medical procedure or the type of medical procedure that is being performed. In another example, a context measure may identify the presence of a tissue type during a medical procedure. In another example, a context measure may identify the presence of one or more fluids, such as biological fluids or non-biological fluids (e.g., wash fluids) during the medical procedure, and may further identify the type of fluid. Each of these examples relates to the image-based identification of information pertaining to the context of the medical procedure.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 400, is to provide tools to the neurosurgeon that will lead to the most informed, least damaging neurosurgical operations. In addition to removal of brain tumours and intracranial hemorrhages (ICH), the navigation system 200 can also be applied to a brain biopsy, a functional/deep-brain stimulation, a catheter/shunt placement procedure, open craniotomies, endonasal/skull-based/ENT, and/or spine procedures.

Figure 7:
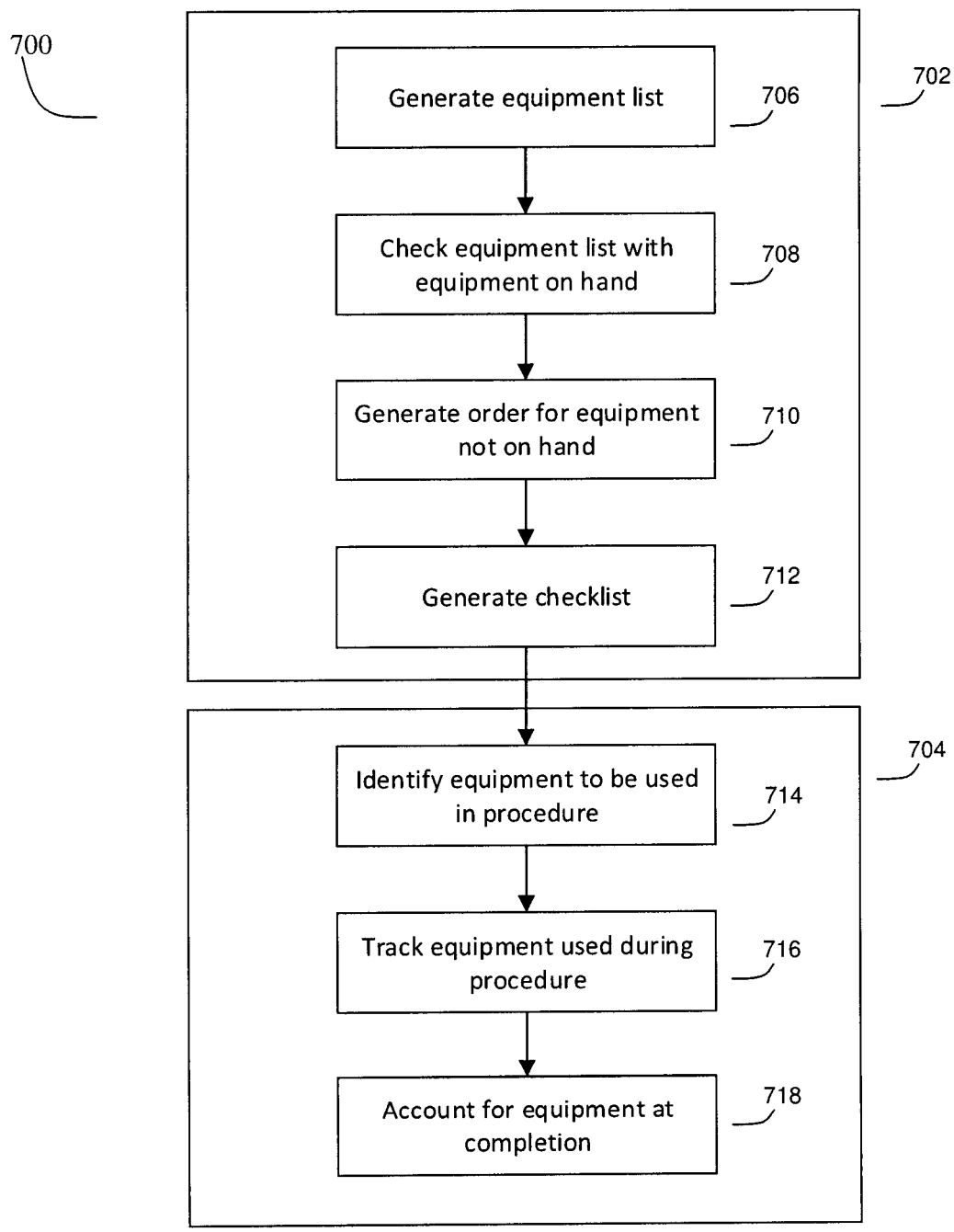
FIG. 7 shows in flow chart form a method 700 of managing equipment for a medical procedure.

Referring to FIG. 7, a flowchart is shown illustrating a method 700 of managing equipment for a medical procedure according to one aspect of the present disclosure. The method 700 may include two portions; a first portion 702 of the method 700 may form part of the planning phase of planning a medical procedure, for example using the planning module 300 shown in FIG. 3. In one example, portion 702 may form an extension of or addition to the planning method 400 shown in FIG. 4. A second portion 704 of the method 700 may form part of the procedure phase of a medical procedure, for example using the medical navigation system 200, shown in FIG. 2.

The first portion 702 of the method 700 includes a first block 706, where an equipment list is generated for a planned medical procedure.

In one example, generation of the equipment list may be performed by a user selecting from a list of tools, the medical navigation system 200 may have a record of which tools are used in the specific procedure type being planned (e.g., based on a saved library) for automatic equipment list generation, or a combination of automatic and manual selection may be used. Selection may also be dependent on the physician performing the surgery, in which case the physician may have input into equipment list selection.

Once a medical procedure has been planned, for example using the planning method 400 and/or the planning module 300, based on the planned medical procedure a list of equipment needed (e.g., a bill of materials) for performing the medical procedure may be generated, for example by the processor 402 executing one or more of the modules 470. The list of equipment needed may include surgical tools, consumables such as gauze or bandages, physical equipment such hospital beds, or any other item needed to perform the planned medical procedure. In one example, the method 700 can be customized according to the design criteria of a particular application to meet the needs of a particular medical facility with respect to the level of detail required in the generated equipment list (e.g., a particular facility may only want to see a list of consumables and tools required). The generated list of needed equipment may include specific identifying information for each piece of equipment needed, such as a bar code (whether one dimensional or two dimensional), an inventory number, a picture of the item, a radio frequency identifier (associated with an RFID tag on the piece of equipment), or any other suitable piece of identifying information to meet the needs of the facility where the method 700 is performed. The specific identifying information for each piece of equipment may further include serializing ability so that two otherwise identical devices (e.g., scissors, scalpels, etc) can be distinguished from each other.

In one example, the specific identifying information may be stored as the identification data 450.

Next, at a block 708, the generated equipment list is checked with equipment on hand at a facility where the medical procedure will be performed. In one example, the planning module 300 on which the portion 702 of method 700 is executed may be connected (e.g., through a network) to a hospital Enterprise Resource Planning (ERP) system. At the block 708, the generated equipment list may be checked with inventory on hand at the facility where the medical procedure will be performed and specific stock may be assigned to the medical procedure to be performed. In one example, stock from the hospital ERP system may be assigned to the particular planned medical procedure and available levels of inventory are updated in the hospital ERP system, which may include interaction with a hospital accounting system that automatically assigns costs to a procedure, updates accounting records, etc.

Next, at a block 710, an order for equipment not on hand at the facility where the medical procedure will be performed may be automatically generated. The generated order may be in the form of a list displayed on a display to a user of the planning module 300, an automatically completed order form to be printed out, or the generated order may be automatically submitted (e.g., through the Internet), for example to a medical supply company. In one example, the lead time on the ordered equipment may be returned via the Internet by the medical supply company so that the medical procedure can be scheduled at a time and date when the needed equipment is expected to be available at the medical facility where the planned procedure will be performed. At the block 710, new consumables may be automatically ordered when the facility runs low on such consumables, reprocessing of sterile instruments may be automatically scheduled, and shared use of limited equipment available at the facility may be scheduled. Again, this may include interaction with a hospital accounting system that automatically assigns costs to a procedure, updates accounting records, etc.

Next, at a block 712, a checklist for equipment setup and configuration (e.g., as determined from the configuration data 452) is automatically generated, to aid in preparation of the medical facility for performing the medical procedure.

The portion 702 of the method 700 may provide for efficient surgical preparation using the generated list of equipment needed. An automatically generated order for needed equipment and/or consumables may offer cost savings to health care providers. Further, the checklist for equipment setup and configuration may reduce setup time at the facility where the medical procedure will be performed. In one example, the generated checklist may be used with the control and processing system 400 and use an input device such as a camera to recognize equipment (e.g., using either computer vision to identify an item or a bar code printed on the item) to verify equipment on hand to ensure that the correct equipment is on hand. In another example, the control and processing system 400 may have a Radio Frequency Identification (RFID scan) sensor coupled to the processor 402 (not shown) and the control and processing system 400 may identify required equipment for a medical procedure using RFID. Identification data used to positively identify equipment may be stored, for example as the identification data 450. In another example, the input device may be an optical camera, a structured light camera, or a stereo camera pair.

Referring again to FIG. 7, once the first portion 702 (e.g., the planning portion) of the method 700 is complete, the second portion 704 (e.g., the procedure portion) is executed when the medical procedure is about to be performed and is being performed.

At a block 714, pieces of equipment to be used in the medical procedure are identified, for example using input from an input device coupled to the processor 402 (FIG. 6). Typically, the block 714 is executed before commencement of the medical procedure, for example when an operating room attendant is preparing an equipment tray of equipment needed for the procedure. Identifying the pieces of equipment to be used in the medical procedure may occur in a number of ways, including using computer vision (e.g., object recognition using the camera 213) for the control and processing unit 400 to recognize tools in the procedure room, using RFID to perform an inventory of equipment placed on a tray, or using optical bar codes on equipment with either an optical bar code scanner or the camera 213 to account for equipment. In one example, each equipment tray in a procedure room may have an RFID tag attached to the tray so that individual trays can be identified. Alternatively, cameras in addition to the camera 213 may be mounted in locations where trays can be easily viewed by the cameras. Once block 714 has been completed, material and equipment needed for the medical procedure should be accounted for, for example by the medical navigation system 200, and the system 200 will know where each piece of equipment is positioned and where in the procedural plan (e.g., generated using the method 350) each piece of equipment will be used.

Next at a block 716, the pieces of equipment being used during the medical procedure are tracked, for example using input from an input device coupled to the medical navigation system 200. During the medical procedure, the block 716 may perform a number of additional functions in addition to simply tracking the equipment as the equipment moves around the procedure room. These additional functions include flagging equipment recognized by the system 200 that is not needed for the medical procedure and providing appropriate warnings or alerts (e.g., using sounds or visual warnings on the displays 205, 211 to alert staff if a tool is being used that is not identified in the generated plan for the medical procedure) and displaying aids to the professionals performing the medical procedure such as showing pictures of the equipment or tools needed at each stage of the medical procedure, for example on the displays 205, 211. In one example, augmented reality may be used to show a projection of a tool needed at a particular stage in a procedure to assist staff in the procedure room in identifying the correct tools. In one example, augmented reality may be implemented using a device similar to a Google Glass.

Next, at a block 718, each of the pieces of equipment is accounted for at completion of the medical procedure using input from the input device. As the medical procedure wraps up, the medical navigation system 200 ensures that all pieces of equipment used in the medical procedure is accounted for. For example, the system 200 may ensure that all tools used during the procedure have been returned to an equipment tray. If all tools have not been returned to an equipment tray, the system 200 may provide appropriate warnings or alerts (e.g., using audible alarms or visual warnings on the displays 205, 211). Once all equipment has been accounted for and is placed in an appropriate position, the method 700 is complete.

In one example, the input device may include the tracking camera 213 or a number of tracking cameras that monitor the area around the medical procedure and use object recognition to track the equipment and tools being used in the medical procedure. However, as described above, any suitable method of tracking the equipment and tools may be used including RFID, bar codes, tracking markers 212 placed on important pieces of equipment or trays, etc.

One aspect of the present description provides an electronic device including a processor, an input device coupled to the processor, a memory coupled to the processor; and a module saved in the memory. The module configures the processor to, during a procedure phase of a medical procedure, identify pieces of equipment to be used in the medical procedure using input from the input device; track the pieces of equipment being used in the medical procedure using input from the input device; and account for each of the pieces of equipment at completion of the medical procedure using input from the input device. Optionally, the module may further configure the processor to: based on a medical procedure plan generated during a planning phase of the medical procedure and prior to the procedure phase: generate an equipment list for completing the medical procedure; check the generated equipment list with equipment on hand at a facility where the medical procedure will be performed; and automatically generate an order for equipment not on hand at the facility where the medical procedure will be performed.

The input device may include a tracking camera, an optical camera, RFID receiver, a structured light camera, or a stereo camera pair.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

What is claimed is:

1. An electronic device comprising:
    a processor;
    an input device comprising a structured light tracking camera coupled with the processor, the structured light tracking camera configured to track at least one of: a tissue, a biological fluid, and a non-biological fluid, and the structured light tracking camera configured to track a plurality of 3D volumes at different resolutions, each 3D volume of the plurality of 3D volumes tracked in relation to at least one of a unique time-stamp and a quality metric, whereby a data structure is provided enabling tracking, during a medical procedure, in relation to at least one of contrast, scale, and time;
    a memory coupled with the processor; and
    a module saved in the memory, the module for configuring the processor, during a procedure phase of a medical procedure, the medical procedure comprising a minimally invasive procedure, to:
    identify pieces of equipment to be used in the medical procedure by using input from the input device;
    track the pieces of equipment being used in the medical procedure by using input from the input device;
    account for each piece of the pieces of equipment at completion of the medical procedure by using input from the input device;
    display, on a display of the electronic device, a visual image of a tool needed at a particular point in the medical procedure;
    based on a medical procedure plan generated during a planning phase of the medical procedure and prior to the procedure phase: generate an equipment list for completing the medical procedure, thereby providing a generated equipment list; check the generated equipment list with equipment that is on hand at a facility where the medical procedure will be performed; and automatically generate an order for equipment that is not on hand at the facility where the medical procedure will be performed; and
    during each medical procedure phase of the medical procedure, identify a tool being handled by using input from the input device; and generate a warning if the identified tool is not the correct tool according to the equipment list generated during the planning phase,
    wherein the tool is intraoperatively configurable by determining at least one context measure associated with the medical procedure, and
    wherein the at least one context measure comprises at least one of: a presence of a tissue having a particular type during the medical procedure, a presence of at least one fluid of a biological fluid and a non-biological fluid, and a fluid having a particular type.

2. The electronic device according to claim 1, wherein the module further configures the processor to: generate a checklist for equipment setup and configuration during preparation of a medical facility for performing the medical procedure.

3. The electronic device according to claim 1, wherein the electronic device further has a radio-frequency identification (RFID) sensor coupled to the processor and at least some pieces of equipment used in the medical procedure are accounted for and tracked using input from the RFID sensor.

4. The electronic device according to claim 1, wherein the module further configures the processor to: generate an output to be transmitted to a hospital accounting system for automatically updating hospital accounting records.

5. A method of managing equipment for a medical procedure, the method including, during a procedure phase of a medical procedure comprising a minimally invasive procedure:
- identifying pieces of equipment to be used in the medical procedure based on input from an input device, the input device comprising a structured light tracking camera, identifying comprising providing the structured light tracking camera configured to track at least one of: a tissue, a biological fluid, and a non-biological fluid, and providing the structured light tracking camera comprising configuring the structured light tracking camera to track a plurality of 3D volumes at different resolutions, each 3D volume of the plurality of 3D volumes tracked in relation to at least one of a unique time-stamp and a quality metric, whereby a data structure is provided enabling tracking, during a medical procedure, in relation to at least one of contrast, scale, and time;
- tracking the pieces of equipment being used in the medical procedure based on input from the input device;
- accounting for each piece of the pieces of equipment at completion of the medical procedure based on input from the input device;
- displaying, on a display, a visual image of a tool needed at a particular point in the medical procedure; and
- during each medical procedure phase of the medical procedure, identifying a tool being handled by using input from the input device; and generating a warning if the identified tool is not the correct tool according to the equipment list generated during the planning phase,
- wherein identifying the tool comprises intraoperatively configuring the tool by determining at least one context measure associated with the medical procedure, and
- wherein determining the at least one context measure comprises determining at least one of: a presence of a tissue having a particular type during the medical procedure, a presence of at least one fluid of a biological fluid and a non-biological fluid, and a fluid having a particular type.

6. The method according to claim 5, wherein the method further comprises, based on a medical procedure plan generated during a planning phase of the medical procedure and prior to the procedure phase: generating an equipment list for completing the medical procedure; checking the generated equipment list with equipment on hand at a facility where the medical procedure will be performed; and automatically generating an order for equipment not on hand at the facility where the medical procedure will be performed.

7. The method according to claim 6, wherein the method further comprises: generating a checklist for equipment setup and configuration during preparation of a medical facility for performing the medical procedure.

8. The method according to claim 5, wherein the input is further received from a radio-frequency identification (RFID) sensor and at least some pieces of equipment used in the medical procedure are accounted for and tracked using input from the RFID sensor.

9. The device of claim 1, wherein the warning comprises at least one of a visual warning and an audible alarm.

10. The device of claim 1,
- wherein the structured light tracking camera is further configured to track at least one of: an identifier and a data element, and
- wherein the at least one context measure further comprises at least one of an identifier, a data element, information that pertains to at least one of the medical procedure, a type of the medical procedure, and a current phase of the medical procedure.

11. The method of claim 5, wherein generating a warning comprises generating at least one of a visual warning and an audible alarm.

12. The method of claim 5,
- wherein the structured light tracking camera is further configured to track at least one of: an identifier and a data element, and
- wherein determining the at least one context measure further comprises determining at least one of: an identifier, a data element, information that pertains to at least one of the medical procedure, a type of the medical procedure, and a current phase of the medical procedure.

* * * * *